(12) United States Patent
Bitenc et al.

(10) Patent No.: US 10,001,501 B2
(45) Date of Patent: Jun. 19, 2018

(54) SYSTEMS AND METHODS FOR AUTOMATED, CUSTOMIZABLE SAMPLE PREPARATION FOR DETECTION OF METABOLITES AND LIPIDS

(71) Applicant: Universal Diagnostics, S.L., Seville (ES)

(72) Inventors: Marko Bitenc, Seville (ES); Kristi Kruusmaa, Seville (ES); Paola Hurtado Castillo, Seville (ES); Ana María Jiménez Girón, Seville (ES); Rosa Argamasilla Martinez, Seville (ES); Andreu Fabregat Rossell, Seville (ES); Antonio Jesus Adsuar Gomez, Seville (ES); Juan Martinez-Barea, Seville (ES); Christian Hense, Seville (ES); Patricia Rodríguez Gómez, Seville (ES)

(73) Assignee: Universal Diagnostics, S. L., Seville (ES)

( * ) Notice: Subject to any disclaimer, the term of this patent is extended or adjusted under 35 U.S.C. 154(b) by 0 days. days.

(21) Appl. No.: 15/395,472

(22) Filed: Dec. 30, 2016

(65) Prior Publication Data
US 2017/0192029 A1    Jul. 6, 2017

Related U.S. Application Data

(60) Provisional application No. 62/273,849, filed on Dec. 31, 2015.

(51) Int. Cl.
*G01N 35/00*    (2006.01)
*G01N 35/02*    (2006.01)
(Continued)

(52) U.S. Cl.
CPC ..... *G01N 35/1074* (2013.01); *G01N 35/0099* (2013.01); *G01N 35/00732* (2013.01);
(Continued)

(58) Field of Classification Search
CPC .......... G01N 2035/00326; G01N 2035/00356; G01N 2035/00445; G01N 2035/00495;
(Continued)

(56) References Cited

U.S. PATENT DOCUMENTS

2003/0199078 A1    10/2003    Kleiber et al.
2006/0210435 A1    9/2006    Alavie et al.
(Continued)

OTHER PUBLICATIONS

International Partial Search Report, PCT/EP2016/082934, 2 pages, dated Mar. 24, 2017.
(Continued)

*Primary Examiner* — Maureen Wallenhorst
(74) *Attorney, Agent, or Firm* — William R. Haulbrook; Ronen Adato; Choate, Hall & Stewart LLP

(57) ABSTRACT

Described herein are automated and customizable sample preparation and analysis systems for detection and quantification of biomarkers (e.g., metabolites and/or lipids) in biological samples (e.g., blood, serum, or plasma) in a clinical setting. The automated systems are controlled by scripts that integrate communication between the components of the sample preparation system. Also described herein are mass spectrometry-based analytical methods featuring efficient system calibration and sample analysis that provide for accurate quantification of a set of markers in biological samples. The methods are capable of automatic high sample throughput in a clinical setting for detection and quantification using a mass spectrometry system and high performance liquid chromatography column.

22 Claims, 9 Drawing Sheets

(51) Int. Cl.
*G01N 35/04* (2006.01)
*G01N 35/10* (2006.01)
*G01N 33/48* (2006.01)

(52) U.S. Cl.
CPC ........... *G01N 35/028* (2013.01); *G01N 35/04* (2013.01); *G01N 35/1002* (2013.01); *G01N 35/1065* (2013.01); *G01N 33/48* (2013.01); *G01N 2035/00326* (2013.01); *G01N 2035/00356* (2013.01); *G01N 2035/00445* (2013.01); *G01N 2035/00495* (2013.01); *G01N 2035/00524* (2013.01); *G01N 2035/00752* (2013.01); *G01N 2035/00762* (2013.01); *G01N 2035/00772* (2013.01); *G01N 2035/0449* (2013.01); *Y10T 436/11* (2015.01); *Y10T 436/111666* (2015.01); *Y10T 436/25* (2015.01); *Y10T 436/2575* (2015.01); *Y10T 436/25125* (2015.01); *Y10T 436/25375* (2015.01)

(58) Field of Classification Search
CPC .......... G01N 2035/00524; G01N 2035/00752; G01N 2035/00762; G01N 2035/00772; G01N 2035/0449; G01N 35/00732; G01N 35/0099; G01N 35/028; G01N 35/04; G01N 35/1002; G01N 35/1065; G01N 35/1074; G01N 33/48; Y10T 436/11; Y10T 436/111666; Y10T 436/24; Y10T 436/25; Y10T 436/25125; Y10T 436/25375; Y10T 436/2575

USPC ..... 436/43, 45, 63, 161, 173, 174, 175, 177, 436/180; 422/63, 67, 70, 72, 501, 509, 422/527, 533

See application file for complete search history.

(56) References Cited

U.S. PATENT DOCUMENTS

| | | | |
|---|---|---|---|
| 2007/0003965 A1 | 1/2007 | Ramsay et al. | |
| 2009/0090856 A1 | 4/2009 | Grant et al. | |
| 2011/0256630 A1* | 10/2011 | Clinton | G01N 35/028 436/48 |
| 2014/0234949 A1 | 8/2014 | Wasson et al. | |
| 2015/0147401 A1 | 5/2015 | Finnie et al. | |
| 2015/0238617 A1* | 8/2015 | Kaplan | A61K 47/42 424/422 |
| 2015/0301002 A1 | 10/2015 | DeWitte et al. | |

OTHER PUBLICATIONS

International Search Report for PCT/EP2016/082934 (Systems and Methods for Automated, Customizable Sample Preparation Tool, Software Script, and Calibration Routine for Detection of Metabolites and Lipids, filed Dec. 30, 2016) issued by ISA/EPA, 7 pages (dated Jun. 28, 2017).
Written Opinion of International Preliminary Examining Authority, PCT/EP2016/082934, (Systems and Methods for Automated, Customizable Sample Preparation Tool, Software Script, and Calibration Routine for Detection of Metabolites and Lipids, filed Dec. 30, 2016) issued by IPEA/EPO, 10 pages, (dated Dec. 14, 2017).

* cited by examiner

SYSTEMS AND METHODS FOR AUTOMATED, CUSTOMIZABLE SAMPLE PREPARATION FOR DETECTION OF METABOLITES AND LIPIDS

CROSS REFERENCE TO RELATED APPLICATION

This application claims the benefit of U.S. Provisional Application No. 62/273,849, filed on Dec. 31, 2015, the content of which is hereby incorporated by reference herein in its entirety.

FIELD

This invention relates generally to systems for biological sample processing and analysis. In particular embodiments, the invention relates to automated preparation and analysis (e.g., via mass-spectrometry) of samples to detect molecules (e.g., metabolites, lipids) from human biofluids (e.g., blood, serum, plasma).

BACKGROUND

Metabolomics is the quantitative measurement of all (or a certain percentage of all, e.g., most) low-molecular-weight metabolites in an organism at a specified time under specific environmental conditions. Metabolites are the end products of cellular processes and their concentrations reflect the functional status of the organism and thus they are closely related to the observed phenotype. Perturbations in biological pathways can amplify the concentration changes of metabolites, making small molecule metabolites very attractive biomarkers of disease detection. The goal of metabolomics is to discover detectable, quantifiable metabolites—e.g., a panel of markers—that serve as evidence of the presence or stage of disease. Thus, by studying metabolic profiles of individuals with certain diseases and conditions, it is the goal of metabolomics to identify panels of metabolites that serve as an effective tool for disease diagnosis, biomarker screening, and characterization of biological pathways.

Two of the most prominent technologies for metabolite detection and quantification are nuclear magnetic resonance (NMR) and mass spectrometry (e.g., coupled to liquid chromatograph—LC-MS, gas chromatograph—GC-MS or direct analysis-DESI, DART). Mass spectrometry identifies and quantifies metabolites after they have been separated from the mixture, e.g., via high performance liquid chromatography (HPLC).

A biological sample is a highly complex mixture with many components. Extraction, detection, identification, and quantification of each of a panel of specific metabolites from biological samples is not a straightforward task. Furthermore, it is important that protocols be well-established in order to accurately and reproducibly extract, identify and quantify a panel of metabolites in a biological sample obtained from a subject. This is particularly important where the purpose of the analysis is the evaluation of a disease diagnostic—variations in how the sample is handled, processed, and analyzed, as well as variations in how the system is calibrated, can affect the result.

There is a need for an automated analytical system that can be used in a clinical setting to extract, identify and quantify a panel of metabolites, e.g., for evaluation of a metabolite-based diagnostic at an accuracy and precision sufficient to maintain an acceptable sensitivity and specificity.

SUMMARY

Described herein are automated and customizable sample preparation and analysis systems for detection and quantification of biomarkers, e.g., metabolites, in biological samples, e.g., blood, serum, or plasma, in a clinical setting. The automated systems are controlled by scripts that integrate communication between the components of the sample preparation system.

Also described herein are mass spectrometry-based analytical methods featuring efficient system calibration and sample analysis that provide for accurate quantification of a set of markers in biological samples. The methods are capable of automatic high sample throughput in a clinical setting for detection and quantification using mass spectrometry system (e.g., ABSciex Triple Quad 4500 MD system) and high performance liquid chromatography column (e.g., Nexera X2 HPLC system from Shimadzu and ACQUITY UPLC BEH C18, 50×2.1 mm, 1.7 µm particle size column from Waters).

In some aspects, the invention is directed to an automated sample handling system for detection and quantification of at least one metabolite biomarker in at least one biological sample, the system comprising: a liquid handling arm for at least one channel air displacement pipette; a plate handler; a code reader; a cooler block shaped and sized to hold the at least one sample; a heater shaker unit; a centrifuge; a metabolite separations/analytics subsystem; a computer processor; and a memory having instructions stored thereon, wherein the instructions, when executed by the computer processor, cause the computer processor to execute a script, wherein the script prescribes processing of the at least one biological sample via coordinated operation of the liquid handling arm, the plate handler; the code reader, the cooler block, the heater shaker unit, and the analytic subsystem. In some embodiments, the at least one biological sample is 96 biological samples.

In some embodiments, the at least one channel air displacement pipette is no more than eight channel air displacement pipettes. In some embodiments, the at least one channel air displacement pipette is for pipetting and mixing. In some embodiments, the plate handler is for transportation of at least one plate from a centrifuge and drier system.

In some embodiments, the code reader is for reading one or more codes, wherein the one or more codes are members selected from the group consisting of: 2D codes, 3D codes, barcodes, and RFIDs. In some embodiments, the code reader is for associating a code with a respective sample and/or corresponding clinical data.

In some embodiments, the heater shaker unit is used to vortex the at least one plate. In some embodiments, the metabolite separations/analytics subsystem comprises an HPLC and a mass spectrometer.

In some embodiments, the script prescribes operation of the metabolite separations/analytics subsystem to perform one or more members selected from the group consisting of (i), (ii), and (iii), as follows: (i) a reverse phase column based method; (ii) a flow injection analysis based method; and (iii) an amide-column based method. In some embodiments, the reverse phase column based method is a member selected from the group consisting of a C18 reverse phase column method, a C18 50 mm reverse phase column method, a C18 100 mm reverse phase column method, a 50 mm reverse phase column method and a 100 mm reverse phase column method. In some embodiments, the one or more members are one or more methods for detection of one or more lipids and/or one or more metabolites.

In some aspects, the invention is directed to a method for automated sample handling for extraction, detection and quantification of at least one metabolite biomarker in at least one biological sample, the method comprising: thawing the at least one biological sample on a cooler block shaped and sized to hold the at least one biological sample; pipetting: (i) the at least one biological sample into at least one plate, (ii) at least one blank sample into the at least one plate, and (iii) at least one quality control sample into the at least one plate; shaking the at least one biological sample; incubating the at least one biological sample on the cooler block; centrifuging the at least one biological sample a first time; removing a first supernatant from the at least one centrifuged biological sample to at least one first analysis plate; applying nitrogen flow to the first supernatant of the at least one biological sample; resuspending the at least one centrifuged biological sample; centrifuging the at least one biological sample a second time; removing a second supernatant from the at least one centrifuged biological sample to at least one second analysis plate; placing the at least one second analysis plate in a metabolite separations/analytics subsystem; and generating at least one analysis report for the at least one sample. In some embodiments, the at least one biological sample is 96 biological samples.

In some embodiments, the thawing the at least one biological sample occurs for at least 1.5 hours. In some embodiments, the at least one biological sample does not leave the cooler block for any time during handling and/or analysis.

In some embodiments, each of the at least one biological sample is identified via a code. In some embodiments, the code is a member selected from a group consisting of: 2D code, 3D code, barcode, and RFID. In some embodiments, each of the at least one biological sample is associated with a code and each code is corresponds to clinical data.

In some embodiments, the at least one biological sample is pipetted into a 96-well plate column-wise. In some embodiments, more than one biological sample is pipetted into the 96-well plate at a time. In some embodiments, at least 8 biological samples are pipetted at a time. In some embodiments, each of the at least one plate is a 96-well plate. In some embodiments, the at least one quality control sample is prepared by mixing at least 5 µL of at least two biological samples.

In some embodiments, at least one plate comprising the at least one biological sample is shaken vigorously for 30 seconds. In some embodiments, the method comprises incubating the at least one biological sample at about 4° C. for at least 15 minutes. In some embodiments, the at least one biological sample is centrifuged at at least 1000 g. In some embodiments, the first time and/or the second time is at least 15 minutes. In some embodiments, the at least one biological sample is transported to the centrifuge by a plate handler. In some embodiments, the nitrogen flow is applied at about room temperature for at least 80 minutes. In some embodiments, the at least one centrifuged biological sample is resuspended with $H_2O$:ACN. In some embodiments, the ratio of $H_2O$:ACN is at least 95:5. In some embodiments, resuspending is sequential aspirating and dispensing. In some embodiments, resuspending the at least one centrifuged biological sample occurs about 50 times.

In some embodiments, centrifuging the at least one biological sample a second time comprises centrifuging at at least 1000 g. In some embodiments, centrifuging the at least one biological sample a second time comprises centrifuging for at least 6 minutes.

In some embodiments, at least 35 µL of supernatant is moved to a final analysis plate. In some embodiments, at least 10 µL of the supernatant from the final analysis plate are transferred to a second final analysis plate where $H_2O$:ACN is added to dilute the supernatant.

In some embodiments, the metabolite separations/analytics subsystem comprises an HPLC and a mass spectrometer. In some embodiments, the at least one first analysis plate and the at least one second analysis plate are stored at 4° C. until an analysis. In some embodiments, the analysis is being placed in the metabolite separations/analytics subsystem.

In some embodiments, the at least one analysis report shows any errors that may have occurred during sample preparation. In some embodiments, the at least one analysis report is generated by a memory having instructions stored thereon, wherein the instructions, when executed by the computer processor, cause the computer processor to execute a script, wherein the script prescribes processing of the at least one biological sample via coordinated operation of the liquid handling arm, the plate handler; the code reader, the cooler block, the heater shaker unit, and the analytic subsystem.

In some embodiments, the method comprises performing one or more members selected from the group consisting of (i), (ii), and (iii), as follows: (i) a reverse phase column based method; (ii) a flow injection analysis based method; and (iii) an amide-column based method. In some embodiments, the reverse phase column based method is a member selected from the group consisting of a C18 reverse phase column method, a C18 50 mm reverse phase column method, a C18 100 mm reverse phase column method, a 50 mm reverse phase column method and a 100 mm reverse phase column method. In some embodiments, the one or more members are one or more methods for detection of one or more lipids and/or one or more metabolites.

In some aspects, the invention is directed to a method of detecting metabolites and/or lipids in a biological sample, the method comprising performing two or more members selected from the group consisting of (i), (ii), and (iii), as follows: (i) a reverse phase column based method; (ii) a flow injection analysis based method; and (iii) an amide-column based method. In some embodiments, the reverse phase column based method is a member selected from the group consisting of a C18 reverse phase column method, a C18 50 mm reverse phase column method, a C18 100 mm reverse phase column method, a 50 mm reverse phase column method and a 100 mm reverse phase column method. In some embodiments, the two or more members are two or more methods for detection of one or more lipids and/or one or more metabolites. In some embodiments, the two or more members is three members or four members.

DEFINITIONS

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Biological Sample": As used herein, the term "biological sample" typically refers to a sample obtained or derived from a biological source (e.g., a tissue or organism or cell culture) of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

"Biomarker": The term "biomarker" is used herein, consistent with its use in the art, to refer to a to an entity whose presence, level, or form, correlates with a particular biological event or state of interest, so that it is considered to be a "marker" of that event or state. To give but a few examples, in some embodiments, a biomarker may be or comprises a marker for a particular disease state, or for likelihood that a particular disease, disorder or condition may develop. In some embodiments, a biomarker may be or comprise a marker for a particular disease or therapeutic outcome, or likelihood thereof. Thus, in some embodiments, a biomarker is predictive, in some embodiments, a biomarker is prognostic, in some embodiments, a biomarker is diagnostic, of the relevant biological event or state of interest. A biomarker may be an entity of any chemical class. For example, in some embodiments, a biomarker may be or comprise a nucleic acid, a polypeptide, a lipid, a carbohydrate, a small molecule, an inorganic agent (e.g., a metal or ion), or a combination thereof. In some embodiments, a biomarker is a cell surface marker. In some embodiments, a biomarker is intracellular. In some embodiments, a biomarker is found outside of cells (e.g., is secreted or is otherwise generated or present outside of cells, e.g., in a body fluid such as blood, urine, tears, saliva, cerebrospinal fluid, etc.

"Comparable": As used herein, the term "comparable" refers to two or more agents, entities, situations, sets of conditions, etc., that may not be identical to one another but that are sufficiently similar to permit comparison there between so that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

"Reference": as used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

"Sample": As used herein, the term "sample" typically refers to a biological sample obtained or derived from a source of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means.

For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Drawings are presented herein for illustration purposes, not for limitation.

DETAILED DESCRIPTION

Throughout the description, where compositions are described as having, including, or comprising specific components, or where methods are described as having, including, or comprising specific steps, it is contemplated that, additionally, there are compositions of the present invention that consist essentially of, or consist of, the recited components, and that there are methods according to the present invention that consist essentially of, or consist of, the recited processing steps.

It should be understood that the order of steps or order for performing certain action is immaterial so long as the invention remains operable. Moreover, two or more steps or actions can be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim. Headers are provided for the convenience of the reader and are not intended to be limiting with respect to the claimed subject matter.

Described herein are automated sample preparation tools for preparation of samples to be evaluated via mass spectrometry for detection and quantification of metabolites in clinical settings. An illustrative sample preparation system has been built and is described herein. The system incorporates components of a liquid handling system, for example, the MICROLAB STAR line STARlet automated liquid handling system from Hamilton Company. As described herein, the illustrative automated system has been created with customized modifications, added system components (e.g., Agilent Vspin Centrifugation system and Porvair Ultravap nitrogen sample drier), and software tools (e.g., developed using Venus Three V4.4 software). A script controls the steps that are automatically conducted on a sample preparation deck starting from controlling the cooler blocks, setting accurate pipetting conditions, and reporting any possible errors. This script is designed to be locked and validated for clinical applications. In addition to the script, the layout of the final sample preparation module has been customized by adding third party items and integrating the drivers to general Hamilton software.

Figure 1:
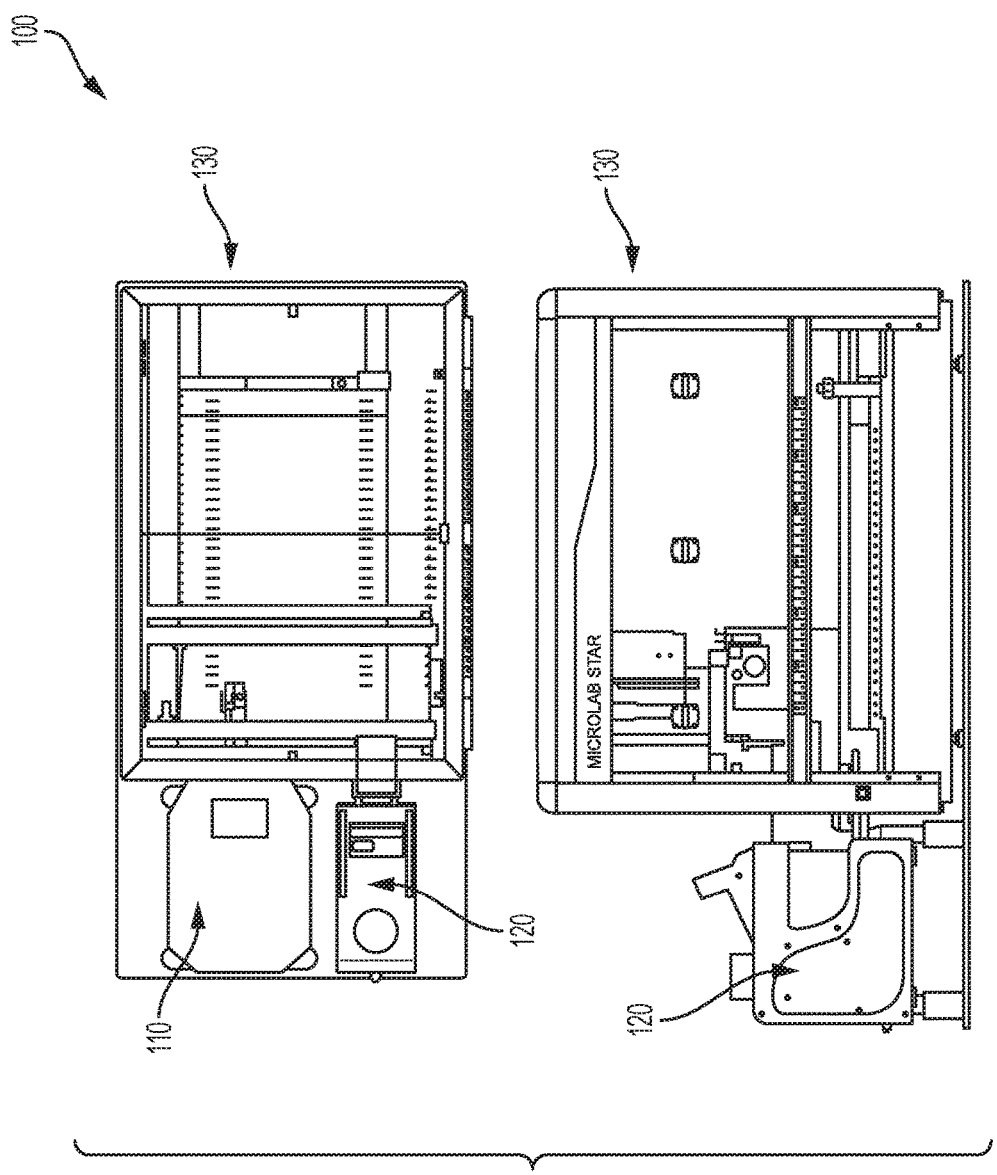
FIG. 1 shows the positioning of an Agilent Vspin Centrifugation system and Porvair Ultravap nitrogen sample drier in an automated sample handling system, according to an illustrative embodiment. Both types of equipment are currently off-deck from the STARlet equipment and are positioned next to the liquid handler system.

FIG. 1 shows integrated sample preparation system 100 consisting of a Hamilton Microlab workstation attached to Agilent Vspin Centrifugation subsystem 110 and Porvair Ultravap nitrogen sample drier 120. In certain embodiments, each of these systems is currently off-deck from the STARlet equipment and is positioned next to the liquid handler system.

Figure 2:
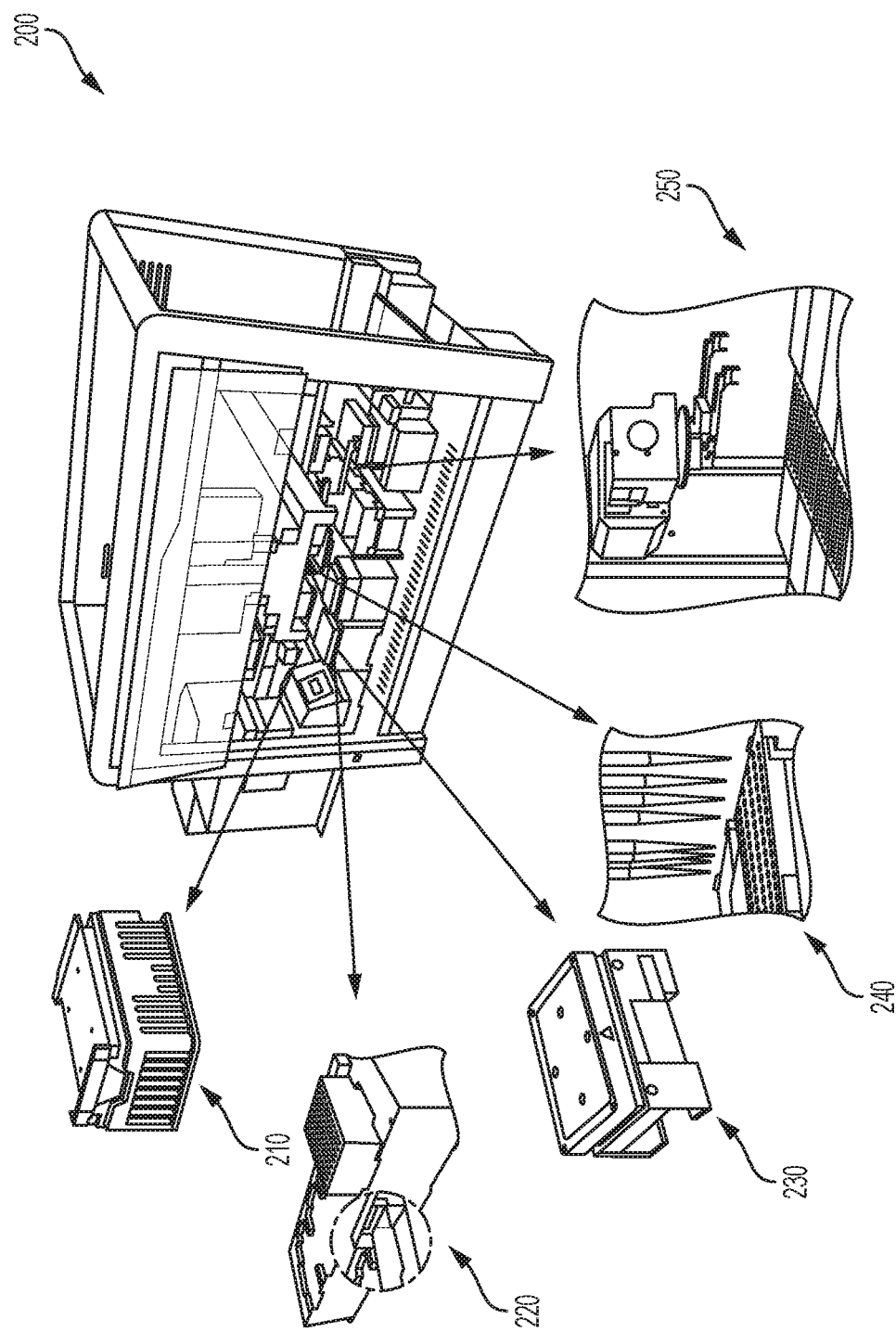
FIG. 2 shows a representation of hardware parts included on-deck of the custom designed STARlet equipment.

FIG. 2 represents the set-up of illustrative custom designed automated sample handling system 200. System 200 includes liquid handling arm for 8-channel air displacement pipettes 240 responsible for pipetting and mixing described in the protocol, iSWAP plate handler system 250 for transportation of the plates over the deck and to outer-deck units of centrifuge and drier system, EasyCode 2D barcode reader 220 for reading 2D codes on each sample vial and for associating codes to clinical samples and corresponding data, two Incheco CPAC Ultraflat cooler blocks 230 that can host 96 samples, and Hamilton Heater Shaker (HHS) Unit 210 for vortexing the sample plates.

Figure 3:
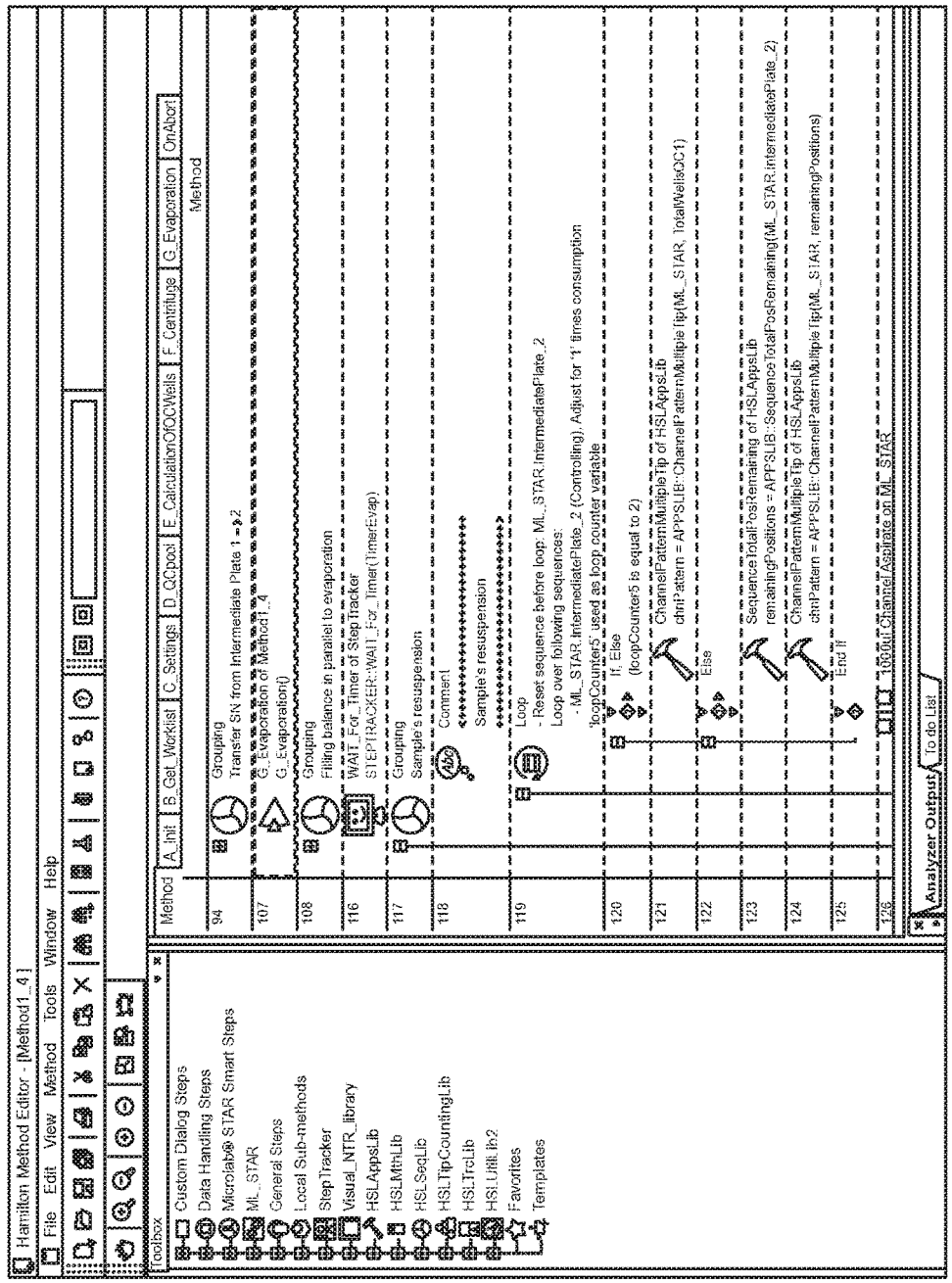
FIG. 3 shows a representation of Venus Three V4.4 software outline.

Referring now to FIG. 3, system 200 may be controlled by Venus Three V4.4. software tool 300 that runs by custom script specifying each step of the automatic process (e.g., keeping the cooler at 4 degrees, e.g., choosing the right liquid classes for each pipetting step so that pipette control for each step could be monitored, etc.). Additionally, error reports and management are implemented into the script alongside with final report for each sample preparation run.

The custom script used to control the automatic process may be comprised of a main methods and/or one or more submethods. For example, the script may comprise a handler method for introducing general test settings and a main method that controls a majority of the sample preparation process, the main method comprising an initialization submethod, a worklist submethod, a settings submethod, a quality control preparation submethod, and a quality control well calculation submethod.

In certain embodiments, the handler method shows a dialog allowing a user to introduce general test settings such as:

a. Number of samples/Transfer this number from default worklist/Prompt for worklist file selection
b. Information about filling balance plates
c. Information about preparation and dispense of QC Pool Samples
d. Read samples 2D barcodes This method calls to the main method using these settings plus a couple of general parameters. General parameters may include a selection to run the full main method or only a partial version of the main method (e.g., the method until evaporation or only from evaporation on); and if the samples will be blank.

The main method is the bulk of sample preparation protocol. It includes all pipetting steps, error handlings and reports. protocol. In certain embodiments, the main method defines the dispension and aspiration numbers, heights, speed/strength depending on a liquid class pipetted. Separate parameters may be defined for each liquid class to avoid tipping of the sample while transporting it over the liquid handler deck. The main method may be written to call to one or more submethods. The use of submethods allows for, in some embodiments, the code to be read and modified more simplistically as well as, in some embodiments, scripting of well-defined modules that may be combined or removed from a particular instance of the main method. In certain embodiments, an initialization submethod, a worklist submethod, a settings submethod, a quality control (QC) preparation submethod, and a QC well calculation submethod are scripted into a main method.

An initialize submethod may be used to initialize different devices such as a liquid handler, cooling blocks (CPACs), an evaporator and a shaker (e.g., an HHS). An exemplary initialization submethod: first initializes the CPACs and waits until temperature in both CPACs equilibrates; then, initializes the liquid handler, shaker, centrifuge and evaporator; secondly, calls a "get worklist" submethod in order to get the number of samples; thirdly, 2D barcodes are read and checked and, if necessary, the Sample Rack is moved to a CPAC; finally, dialogs for sample thawing and calculations for tips and volumes are presented. The initialization submethod may be used to check for a sufficient number of tips according to defined work list. In some embodiments, generic barcodes are also assigned to each plate (e.g., intermediate plate 1, 2 and final plate and final plate 2).

In some embodiments, an off-deck manual centrifuge is used such that any centrifugation steps in automatic sample preparation procedures are handled manually, in which case the initialization submethod does not initialize a centrifuge. In certain embodiments, the equilibration temperature for the CPACs is 4° C.

A "get worklist" submethod reads number and name of samples from input given by the user. In certain embodiments, input is given by selecting a Microsoft Excel file in a predefined path in a computer. In general, Excel files need to be prepared manually before starting the automated sample preparation process. In some embodiments, Number of samples can be introduced manually. If the number of samples is introduced manually, generic barcodes are generated from the number of tubes loaded on the sample rack. Lastly, sample barcodes are assigned to the tubes.

A settings submethod is used to provide selection of settings for different parameters in the protocol. Exemplary settings that may be selected as part of the settings submethod are: settings for manual centrifugation and evaporation, incubation settings, centrifugation settings (if it is not manual), pipetting settings, evaporation settings, and mapping report settings. For example, incubation settings may include incubation time. For example, centrifugation settings may include centrifugation run times. For example, pipetting settings may include MetOH: IS volume, sample volume, mixing cycles, supernatant volume, supernatant aspiration height from the bottom, resuspension volume, resuspension cycles and speed, and general aspiration and dispension cycles, speed and height. For example, evaporation settings may include evaporation distance (e.g., as part of a 5-step process where higher values correspond to deeper inside the plate), evaporation gas flow for each step, temperature for each step, and time for each step. For example, mapping report settings may define report outputs for each step in the main method.

A QC preparation submethod is meant for preparing QC pools. In certain embodiments, it is designed to take 5 µl of each sample and dispense them in an empty tube. A summary and a mapping report of this step may be recorded for future reference. Finally, the submethod may comprise the step of shaking the Sample Rack.

A QC well calculation submethod adjusts all plate filing and movement sequences to the number of samples. In certain embodiments, the QC well calculation submethod also generates arrays of barcodes and wells to be dispensed. The QC well calculation submethod defines arrays that are a template for the way the samples, blanks and controls should be pipetted into plates during a work-flow. The use of defined arrays allows every mapping report generated after each pipetting to check to see what wells were excluded.

Figure 4:
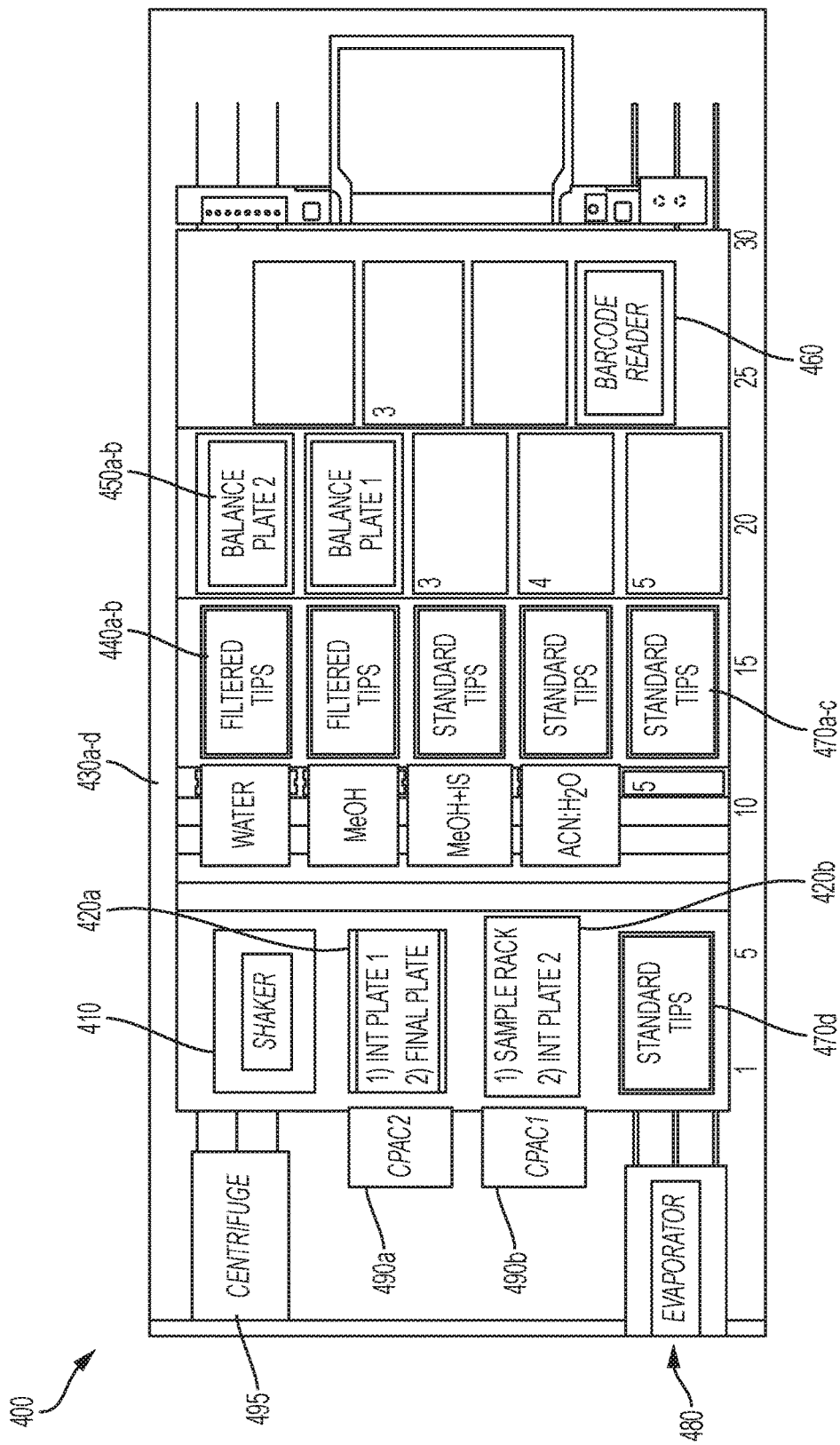
FIG. 4 shows a liquid handler deck layout for starting the sample preparation process, according to an illustrative embodiment of the invention.

The following is an exemplary sample protocol work-flow combining automated sample preparation using the automated system described hereinabove with mass spectrometry-based analysis (e.g., LC-MS/MS), described in more detail below. In certain embodiments, sample protocol work-flows (e.g., the following exemplary sample protocol work-flow) are controlled by a script method that functions similarly to the main method described herein above. In some embodiments, the work flow may be handled automatically by a script method such that after initialization and parameter input, the workflow proceeds without additional action required of an operator. A sample protocol work-flow may additionally comprise one or more initiation steps, such as switching on one or more of a liquid handler system, a centrifuge, a cooling block (e.g., an Inheco CPAC unit), a nitrogen generator, and an evaporator. A sample protocol work-flow may additionally comprise refilling water and/or solvent (e.g., organic solvents such as methanol) containers and/or placing or replacing labeled plates for use during the protocol. For example, a new plate labeled as "Intermediate plate 1" may be placed in or on a cooling block. An exemplary liquid handler deck layout immediately prior to starting the sample preparation process is shown in FIG. 4. Liquid handler deck 400 has shaker unit 410, sample plates 420*a-b*, solvent reservoirs 430, filtered tip banks 440*a-b*, balance plate holders 450 (two out of five positions are occupied with plates), barcode reader 460, standard tip banks 470*a-c*, standard tip bank 470*d*, evaporator 480, CPACs 490*a-b*, and centrifuge 495. The exemplary sample protocol work-flow consists of steps of:

1) Provide inputs for test settings. In some embodiments, a user is provided inputs for selection for the following options:
 a) Introduce number of samples
 b) Get this number from default worklist
 c) Prompt for worklist file selection
 d) Fill balance plates 2) Prepare and dispense a quality control (QC) pool of Samples.
3) Read 2D barcodes of the samples.
4) Evaluate the cooling block (CPAC) temperature. In certain embodiments, the temperature must be at 4° C.
5) Initialize the liquid handler (LH), evaporator and shaker.
6) Fill custom dialog to load samples on the CPAC 1.
7) Timer for thawing samples is set to 90 minutes. In some embodiments, the thawing of the samples can be stopped prematurely in case less than 80 samples are used and samples thaw faster.
8) Custom dialog appears for checking if samples are completely thawed. If they are still frozen, user can set a new time for continuing the thawing up process.
9) Custom dialog appears for filling tips and reagents 1 (MeOH+internal standards (IS)) and 2 (Water:ACN).
10) Custom dialog appears for tips initial position settings.
11) Sample rack is shaken for 30 seconds at 600 rpm.
12) (Optional) QCs are prepared by aspiration of 5 µL of each sample and mixed them together in a separate tube. At the end of this process, sample rack is shaken again for 30 seconds at 600 rpm
13) 300 µL Reagent 1 are dispensed in each well of Intermediate Plate 1
    In some embodiments, tips are conditioned using Methanol. Methanol is pipetted with the tips for couple of times. This avoids dripping of the reagent 1 while transporting it to the tubes. Same tips are used for filling the full plate with 300 µl of Reagent 1.
14) 50 µL from each tube of Samples rack (blank, sample or QC) is dispensed.
    Before aspirating, LH homogenizes samples mixing 50 µL for 5 times
    After dispensation, it is mixed by 5 cycles of aspiration and dispensation. In certain embodiments, the mixing volume is 200 µL.
    Sample error handling: at the end of the sample pipetting step, a custom dialog appears to inform the user that samples were not well pipetted. User has 4 options:
    a) Transfer samples with error manually—Those samples will be considered for next pipetting steps
    b) Skip samples with error—Those samples will not be considered for next pipetting steps
    c) Retry samples with error—LH will retry to pipette those samples again
    d) Abort the method
15) Custom dialog appears for putting a seal mat on Intermediate plate 1. An email is sent to the user.
16) Intermediate plate 1 is shaken for 30 seconds at 1200 rpm
17) Incubation occurs for 15 minutes in the CPAC 2. In certain embodiments, incubation occurs at 4° C.
18) (Process in parallel with step 17) Balance plate 1 is filled with water.
    Volume per well can be 350 µL, 300 µL or 0 µL depending if the equal well in Intermediate Plate 1 has reagent 1 and sample, only reagent 1 (e.g., if sample was discarded in a previous step) or it is empty (no sample to prepare in that well).
19) Custom dialog appears for centrifugation and plate exchange in CPAC 1.
    Intermediate Plate 1 must be centrifuged for 10 minutes at 6168 times gravity at 10° C. on manual centrifuge or 30 minutes at 1000 times gravity at RT with an Agilent Vspin.
    Sample rack must be replaced for Intermediate Plate 2. An email is sent to the user
20) Custom dialog appears for removing the seal mat from Intermediate Plate 1. An email is sent to the user.
21) Transference of 150 µL supernatant from Intermediate Plate 1 to Intermediate Plate 2. In certain embodiments, tips are conditioned using Methanol before each transference.
    After dispensation, tips are moved down over the well one more time to avoid any residual drops and are then discarded.
22) Intermediate Plate 2 is evaporated for 80 minutes using a nitrogen flow of 75 L/min at 25° C. Evaporator's lift moves deeper inside the plate during the evaporation process. In certain embodiments, lift starts at 43.0 mm high and it ends at 48.5 mm.
23) (Process in parallel with step 22) Balance plate 2 is filled in with water.
    Volume per well can be 50 µL or 0 µL depending if there is or not sample in the equal well in Intermediate Plate 2.
24) Resuspension of dried samples in 50 µL Reagent 2. After dispensation of Reagent 2, samples are resuspended by 50 cycles of aspiration and dispensation. In certain embodiments, the mixing volume is 40 µL.
25) Custom dialog for putting a seal mat on Intermediate Plate 2. An email is sent to the user.
26) Intermediate plate 2 is shaken for 30 seconds at 1100 rpm.
27) Custom dialog is presented for manual centrifugation and plate exchange in CPAC 2.
    Intermediate Plate 2 must be centrifuged for 6 minutes at 6168 times gravity and 10° C. with manual centrifuge or 15 minutes at 1000 times gravity and RT with an Agilent Vspin.
28) Intermediate Plate 1 must be replaced for Final Plate. An email is sent to the user.
29) Custom dialog is presented for removing the seal mat from Intermediate Plate 2. An email is sent to the user.
30) 35 µL supernatant is transferred from Intermediate Plate 2 to Final Plate.
31) (Optional) 10 µL of the supernatant from new plate are transferred further to another plate where 90 µL of $H_2O$:ACN is added to dilute the sample for Final Plate 2.
32) Custom dialog is presented with a summary of the process.

The following is an additional exemplary sample protocol work-flow combining automated sample preparation using the automated system described hereinabove with mass spectrometry-based analysis, e.g., LC-MS/MS, described in more detail below.

1) Thaw up all samples on Inheco cooler block for 1.5 h. In certain embodiments, the original aliquots should not leave the cooler block at any time of the sample preparation process.
2) All sample vials carry 2-D barcode on the bottom of the vial. Hamilton Starlet unit is equipped with 2-D barcode reader that reads the information from each vial and stores the vial position in the report that then follows the preparation of each sample.
3) 50 µL of sample is pipetted from initial 2-D barcoded vial into 96-well plate column-wise 8 samples at the time starting from column 3.
4) 1st column includes blank samples and blank samples with standards.
5) 2nd column comprises QC (quality control) samples that are prepared by mixing 5 µL of each initial samples.

6) Once the 96-well plate is filled with samples and controls 300 μL of MetOH including internal standards of the molecules of interest is added and mixed by aspirating and dispensing for 5 times.
7) Plate is then moved to shaker unit and vigorously shaken for 30 seconds
8) Plate is moved back to original location and incubated at 4° C. on CPAC2 for 15 minutes.
9) Meanwhile a counter-balance plate is filled with 350 μL of Water and transported to Agilent Vspin centrifuge.
10) Analysis plate is moved to Agilent Vspin centrifuge after incubation and centrifuged for 30 min at 1000 g.
11) Plate is transported back to original spot after centrifugation and 150 μL of supernatant from each well is pipetted into new analysis plate.
12) Supernatant bearing plate is transported to Povair ultra-vaporator system and nitrogen flow is applied to each well at room temperature for 80 minutes.
13) Meanwhile a counter-balance plate is removed from Agilent centrifugation system and existing liquid is aspirated and 50 μL of water is dispensed into the plate.
14) Plate is transported back to Agilent centrifugation system.
15) Sample plate is transported back to the deck after evaporation and 50 μL of $H_2O$:ACN 95:5 concentration is applied to each well by dispensing and aspirating 50 times.
16) Resuspended plate is transported to Agilent Vspin and centrifugation is applied at 1000 g for 15 minutes.
17) Samples plate is transported back on deck after centrifugation and 35 μL of supernatant is transported to new plate.
18) 10 μl of the supernatant from new plate are transferred further to another plate where 90 μl of $H_2O$:ACN is added to dilute the sample for FIA experiment.
19) 2 final analysis plates are then placed at 4° C. till analysis or are directly placed in mass spectrometry analysis system.
20) Analysis report will be generated for each sample showing any errors that might have occurred during the sample preparation.

Figure 5:
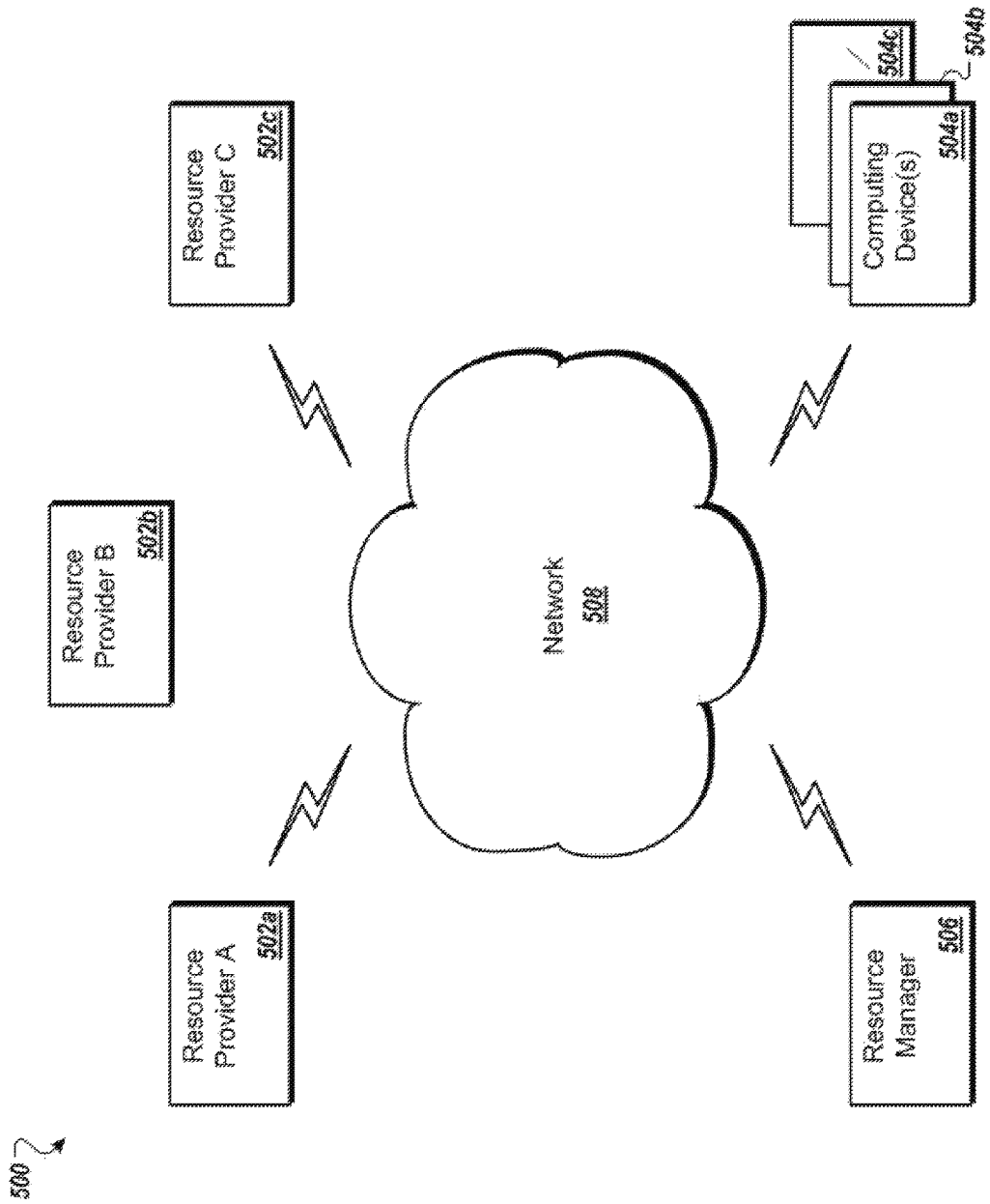
FIG. 5 is a block diagram of an example network environment for use in the methods and systems for analysis of spectrometry data, according to an illustrative embodiment.

The sample preparation protocol workflows described herein (e.g., the workflows described above) may be controlled using script methods run from a computer that is either local or remote to the preparation system. FIG. 5 shows an illustrative network environment 500 for use in the methods and systems described herein. In brief overview, referring now to FIG. 5, a block diagram of an exemplary cloud computing environment 500 is shown and described. The cloud computing environment 500 may include one or more resource providers 502a, 502b, 502c (collectively, 502). Each resource provider 502 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 502 may be connected to any other resource provider 502 in the cloud computing environment 500. In some implementations, the resource providers 502 may be connected over a computer network 508. Each resource provider 502 may be connected to one or more computing device 504a, 504b, 504c (collectively, 504), over the computer network 508.

The cloud computing environment 500 may include a resource manager 506. The resource manager 506 may be connected to the resource providers 502 and the computing devices 504 over the computer network 508. In some implementations, the resource manager 506 may facilitate the provision of computing resources by one or more resource providers 502 to one or more computing devices 504. The resource manager 506 may receive a request for a computing resource from a particular computing device 504. The resource manager 506 may identify one or more resource providers 502 capable of providing the computing resource requested by the computing device 504. The resource manager 506 may select a resource provider 502 to provide the computing resource. The resource manager 506 may facilitate a connection between the resource provider 502 and a particular computing device 504. In some implementations, the resource manager 506 may establish a connection between a particular resource provider 502 and a particular computing device 504. In some implementations, the resource manager 506 may redirect a particular computing device 504 to a particular resource provider 502 with the requested computing resource.

Figure 6:
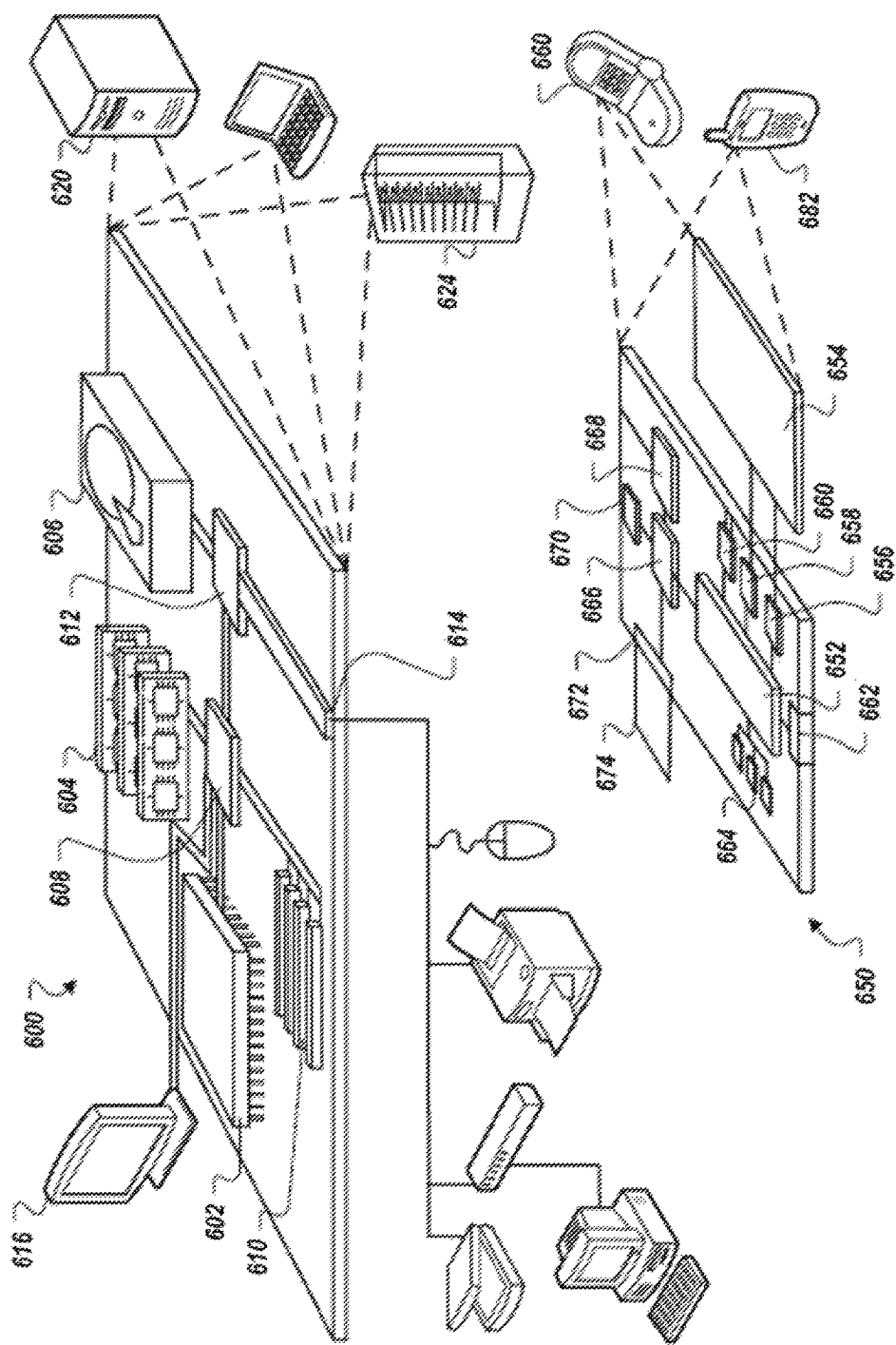
FIG. 6 is a block diagram of an example computing device and an example mobile computing device, for use in illustrative embodiments of the invention.

FIG. 6 shows an example of a computing device 600 and a mobile computing device 650 that can be used in the methods and systems described in this disclosure. The computing device 600 is intended to represent various forms of digital computers, such as laptops, desktops, workstations, personal digital assistants, servers, blade servers, mainframes, and other appropriate computers. The mobile computing device 650 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 600 includes a processor 602, a memory 604, a storage device 606, a high-speed interface 608 connecting to the memory 604 and multiple high-speed expansion ports 610, and a low-speed interface 612 connecting to a low-speed expansion port 614 and the storage device 606. Each of the processor 602, the memory 604, the storage device 606, the high-speed interface 608, the high-speed expansion ports 610, and the low-speed interface 612, are interconnected using various busses, and may be mounted on a common motherboard or in other manners as appropriate. The processor 602 can process instructions for execution within the computing device 600, including instructions stored in the memory 604 or on the storage device 606 to display graphical information for a GUI on an external input/output device, such as a display 616 coupled to the high-speed interface 608. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 604 stores information within the computing device 600. In some implementations, the memory 604 is a volatile memory unit or units. In some implementations, the memory 604 is a non-volatile memory unit or units. The memory 604 may also be another form of computer-readable medium, such as a magnetic or optical disk.

The storage device 606 is capable of providing mass storage for the computing device 600. In some implementations, the storage device 606 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 602), perform one or more methods, such as those described above. The instructions can also be stored by one or more storage devices such as computer- or machine-readable mediums (for example, the memory 604, the storage device 606, or memory on the processor 602).

The high-speed interface 608 manages bandwidth-intensive operations for the computing device 600, while the low-speed interface 612 manages lower bandwidth-intensive operations. Such allocation of functions is an example only. In some implementations, the high-speed interface 608 is coupled to the memory 604, the display 616 (e.g., through a graphics processor or accelerator), and to the high-speed expansion ports 610, which may accept various expansion cards (not shown). In the implementation, the low-speed interface 612 is coupled to the storage device 606 and the low-speed expansion port 614. The low-speed expansion port 614, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 600 may be implemented in a number of different forms, as shown in the figure. For example, it may be implemented as a standard server 620, or multiple times in a group of such servers. In addition, it may be implemented in a personal computer such as a laptop computer 622. It may also be implemented as part of a rack server system 624. Alternatively, components from the computing device 600 may be combined with other components in a mobile device (not shown), such as a mobile computing device 650. Each of such devices may contain one or more of the computing device 600 and the mobile computing device 650, and an entire system may be made up of multiple computing devices communicating with each other.

The mobile computing device 650 includes a processor 652, a memory 664, an input/output device such as a display 654, a communication interface 666, and a transceiver 668, among other components. The mobile computing device 650 may also be provided with a storage device, such as a micro-drive or other device, to provide additional storage. Each of the processor 652, the memory 664, the display 654, the communication interface 666, and the transceiver 668, are interconnected using various buses, and several of the components may be mounted on a common motherboard or in other manners as appropriate.

The processor 652 can execute instructions within the mobile computing device 650, including instructions stored in the memory 664. The processor 652 may be implemented as a chipset of chips that include separate and multiple analog and digital processors. The processor 652 may provide, for example, for coordination of the other components of the mobile computing device 650, such as control of user interfaces, applications run by the mobile computing device 650, and wireless communication by the mobile computing device 650.

The processor 652 may communicate with a user through a control interface 658 and a display interface 656 coupled to the display 654. The display 654 may be, for example, a TFT (Thin-Film-Transistor Liquid Crystal Display) display or an OLED (Organic Light Emitting Diode) display, or other appropriate display technology. The display interface 656 may comprise appropriate circuitry for driving the display 654 to present graphical and other information to a user. The control interface 658 may receive commands from a user and convert them for submission to the processor 652. In addition, an external interface 662 may provide communication with the processor 652, so as to enable near area communication of the mobile computing device 650 with other devices. The external interface 662 may provide, for example, for wired communication in some implementations, or for wireless communication in other implementations, and multiple interfaces may also be used.

The memory 664 stores information within the mobile computing device 650. The memory 664 can be implemented as one or more of a computer-readable medium or media, a volatile memory unit or units, or a non-volatile memory unit or units. An expansion memory 674 may also be provided and connected to the mobile computing device 650 through an expansion interface 672, which may include, for example, a SIMM (Single In Line Memory Module) card interface. The expansion memory 674 may provide extra storage space for the mobile computing device 650, or may also store applications or other information for the mobile computing device 650. Specifically, the expansion memory 674 may include instructions to carry out or supplement the processes described above, and may include secure information also. Thus, for example, the expansion memory 674 may be provided as a security module for the mobile computing device 650, and may be programmed with instructions that permit secure use of the mobile computing device 650. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 652), perform one or more methods, such as those described above. The instructions can also be stored by one or more storage devices, such as one or more computer- or machine-readable mediums (for example, the memory 664, the expansion memory 674, or memory on the processor 652). In some implementations, the instructions can be received in a propagated signal, for example, over the transceiver 668 or the external interface 662.

The mobile computing device 650 may communicate wirelessly through the communication interface 666, which may include digital signal processing circuitry where necessary. The communication interface 666 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 668 using a radio-frequency. In addition, short-range communication may occur, such as using a Bluetooth®, Wi-Fi™, or other such transceiver (not shown). In addition, a GPS (Global Positioning System) receiver module 670 may provide additional navigation- and location-related wireless data to the mobile computing device 650, which may be used as appropriate by applications running on the mobile computing device 650.

The mobile computing device 650 may also communicate audibly using an audio codec 660, which may receive spoken information from a user and convert it to usable digital information. The audio codec 660 may likewise generate audible sound for a user, such as through a speaker, e.g., in a handset of the mobile computing device 650. Such sound may include sound from voice telephone calls, may include recorded sound (e.g., voice messages, music files, etc.) and may also include sound generated by applications operating on the mobile computing device 650.

The mobile computing device 650 may be implemented in a number of different forms, as shown in the figure. For example, it may be implemented as a cellular telephone 680. It may also be implemented as part of a smart-phone 682, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Mass Spectrometry Method for Analyzing LC Markers

Described herein are mass spectrometry methods for targeted analysis of markers (e.g., metabolites and/or lipids) with ABSciex Triple Quad 4500 MD system together with Nexera X2 HPLC system from Shimadzu. It is contemplated that one of ordinary skill in the art could use any combination of known mass spectrometers, HPLC systems, and/or particle size columns that provide similar and/or equivalent functionality and are able to be integrated together. In certain embodiments, this method is used for marker separation, detection and quantification.

Method Calibrators and Protocol

The methods described herein may use two calibration curves (e.g., 1 with eight levels of concentration and another with 6 levels of concentration) as described below, as well as a blank sample, and zero sample alongside experimental samples. In certain embodiments, a calibration curve and blank and zero samples are processed together with analysis samples. In certain embodiments, two calibration curves are prepared to quantify all markers of the panel. Calibrators can be prepared freshly every day to assure appropriate reproducibility.

The blank matrix can be a solution of 2% BSA (bovine serum albumin) in PBS (phosphate buffered saline). Preparation of STD 8 (the highest concentration standard) is described in Tables 1-2. Alternatively, the blank matrix can be SeraSub®, which is a synthetic polymer in buffered solution which is physically equivalent to serum and plasma with respect to: specific gravity, viscosity and osmolality.

All experimental samples, quality control samples and blank standards are prepared as one analysis set and analyzed in one analysis run. Blank samples and QC samples are analyzed every 10 samples for evaluating stability of the system over long run and applying normalization for the samples.

Table 1 shows an example of how STD 8 from 8-level calibration curve can be prepared without internal standards (IS) (e.g., to prepare the rest of calibrators or standards) using a BSA solution for the blank matrix.

TABLE 1

|  | µL |
| --- | --- |
| 2% BSA in PBS | 312 |
| POOL of external standards | 236.98 |
| Methanol/H2O (60:40) | 51.02 |
| % BSA-PBS | 52% |

Table 2 shows an example of preparation of STD 8 with IS.

TABLE 2

|  | µL |
| --- | --- |
| 2% BSA in PBS | 303.02 |
| POOL of internal standards | 60 |

TABLE 2-continued

| | µL |
|---|---|
| POOL of markers | 236.98 |
| % BSA-PBS | 51% |

An example of how to prepare the remaining standards (e.g., STD 7-STD1) with internal standards is shown below in Table 3.

TABLE 3

| µL | STD 7 | STD 6 | STD 5 | STD 4 | STD 3 | STD 2 | STD 1 |
|---|---|---|---|---|---|---|---|
| 2% BSA in PBS | 17.5 | 37 | 56.48 | 75.99 | 88.99 | 95.49 | 98.75 |
| POOL of internal standards | 20 | 20 | 20 | 20 | 20 | 20 | 20 |
| Methanol/H2O (60:40) | 0 | 18 | 35.98 | 53.99 | 65.99 | 71.99 | 74.99 |
| STD 8 without IS | 162.5 | 125 | 87.53 | 50.02 | 25.01 | 12.50 | 6.25 |

Analysis by LC-MS/MS

A range of methods may be used to conduct mass spectrometry analysis depending on the biological and/or chemical nature of the marker being analyzed. For example, one may use an amide-column based metabolite detection method for detecting highly polar compounds, a "C18 50 mm reverse phase column" based metabolite detection method for more non-polar compounds, an FIA-based direct infusion injection based method for detecting fatty acid markers, or a "C18 100 mm reverse phase column" based method for detecting lipids. In certain embodiments, multiple mass spectrometry analysis methods may be utilized for detection/quantification of biomarkers prepared using a single automated sample preparation workflow. For example, multiple related, but distinct columns and/or methods may be used to analyze a particular biological sample (e.g., a column-based and flow injection analysis-based method may be used conjunctively). Described below are details of these four exemplary LC-MS/MS methods.

Exemplary "C18 50 mm Reverse Phase Column Based" Method

Figure 7:
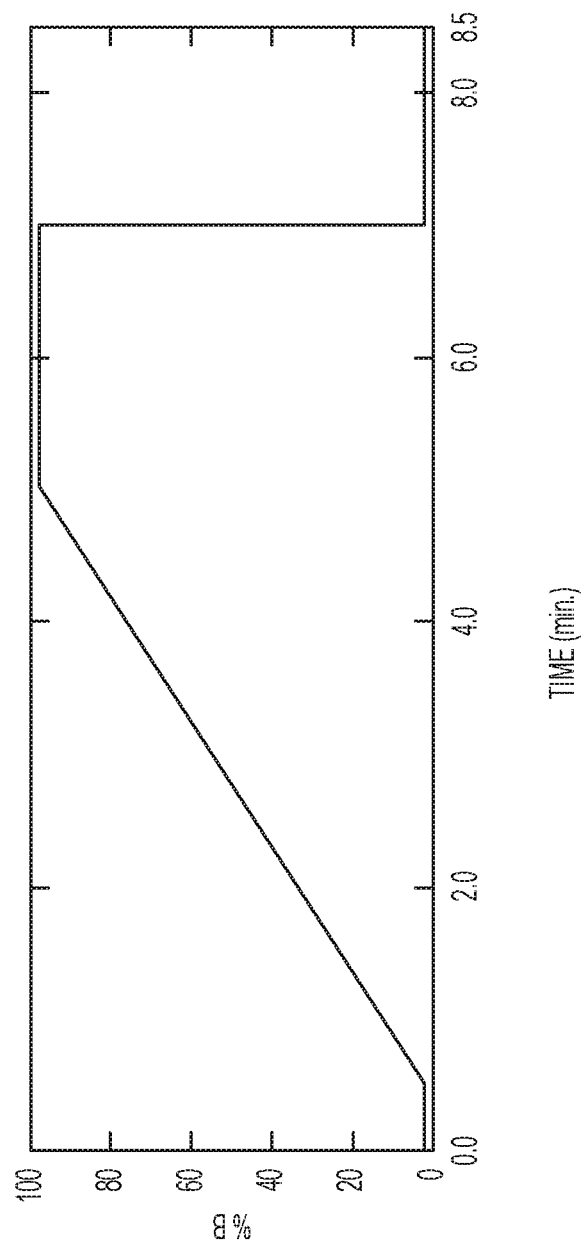
FIG. 7 is a graph of a gradient curve used in the LC part of an LC-MS/MS analysis for detection of metabolites and lipids in biological samples, according to an illustrative embodiment.

The following are the HPLC conditions used in an illustrative embodiment of an LC-MS/MS analysis protocol for markers using a "C18 50 mm reverse phase column" based method:

Column used: ACQUITY UPLC BEH C18, 50×2.1 mm, 1.7 µm particle size column from Waters
Pre-column used: VanGuard Acquity UPLC BEH C18 1.7 µm
Solvents used:
  A: 100% water and 0.1% Formic acid
  B: 100% acetonitrile and 0.1% Formic acid
Cleaning solution: 50% methanol and 50% water
Injection volume: 1 µL
Temperatures:
  Column Temperature: 40° C.
  Auto sampler Temperature: 10° C.
Flow rate: 0.5 mL/min
Times:
  Run time: 7 min
  Equilibration time: 1.5 min
Gradient used:
  Starting conditions. 98% A-2% B
  The rest of the gradient curve is shown in FIG. 7

The following is a description of the MS conditions used in this illustrative LC-MS/MS analysis protocol.

General conditions for the MS part of the analysis run are described in Table 4.

TABLE 4

| ESI + | | ESI − | | |
|---|---|---|---|---|
| CUR: | 50.00 | CUR: | 50.00 | MRM detection window: 40 sec |
| IS: | 5000.00 | IS: | 4500.00 | Target Scan Time: 0.1 sec |

TABLE 4-continued

| ESI + | | ESI − | | |
|---|---|---|---|---|
| TEM: | 500.00 | TEM: | 500.00 | Resolution Q1: Unit |
| GS1: | 60.00 | GS1: | 60.00 | Resolution Q3: Unit |
| GS2: | 65.00 | GS2: | 65.00 | Settling Time: 58 msec |
| CAD: | −2.00 | CAD: | −2.00 | MR Pause: 5 msec |
| EP | 10.00 | EP | 10.00 | |

Parameters Used:

REGRESSION equation for concentration calculation: $y=a*x+b$ ($y$=concentration, $a$=area, $b$=linear fit and $1/x$ weighting. In certain embodiments, the weighting is used to compensate for deviation in the lower values due to the highest ones. The weighting may be calculated as an experimental value.)
SMOOTH: 1
NOISE: 95%
OUTLIER SETTINGS:
  Maximum accuracy tolerance for Standards 15% except for LLOQ (20%)
  Maximum accuracy tolerance for QC 15%
  Ion ratio tolerance 30%

Exemplary FIA (Flow Injection Analysis)-based Method

The following are LC and MS conditions for an illustrative FIA-based analysis for detection of markers. First, the following are the LC conditions:

Column: none
Solvent:
  A: methanol
  B. methanol, 1 mM ammonium formiate
Injection volume 2 µL
Auto sampler temperature set to 10° C.
ANALYSIS METHOD: Isocratic, 100% B
Flow rate: 0.36 mL/min
Run time: 1 min
CLEANING METHOD (each 10 samples): Isocratic, 100% A
  Flow rate: 0.5 mL/min
  Run time: 2 min
Instrument maintenance:
  During the batch, for each of 10 samples, inject MeOH with the following cleaning method:

After every batch: flush the tubing with 50% water, 50% isopropanol for 20 min at 0.5 mL/min
Then with 50% water, 50% MeOH
Injection conditions are shown in Table 5

TABLE 5

| Time (min) | Flow (ml/min) |
|---|---|
| 0 | 0.05 |
| 1.6 | 0.05 |
| 2.4 | 0.2 |
| 2.8 | 0.2 |
| 3 | 0.05 |

The following equation was used to compute relative quantity of a given marker:

Result=(response of anAnalyte*isotope correctedAnalyte*amount IS)/response IS*isotope corrected IS The following is a description of the MS conditions used in this illustrative LC-MS/MS analysis protocol.

General conditions for the MS part of the analysis run are described in Table 6.

TABLE 6

| ESI + | | |
|---|---|---|
| CUR: | 40 | Non-scheduled MRM |
| IS: | −4500 | Dwell Time: 100 msec |
| TEM: | 550 | Resolution Q1: Unit |
| GS1: | 60 | Resolution Q3: Unit |
| GS2: | 65 | MR Pause: 5 msec |
| CAD: | 5 | |
| EP: | −10 | |

Exemplary "C18 100 mm Reverse Phase Column Based" Method for Lipid Detection

Figure 8:
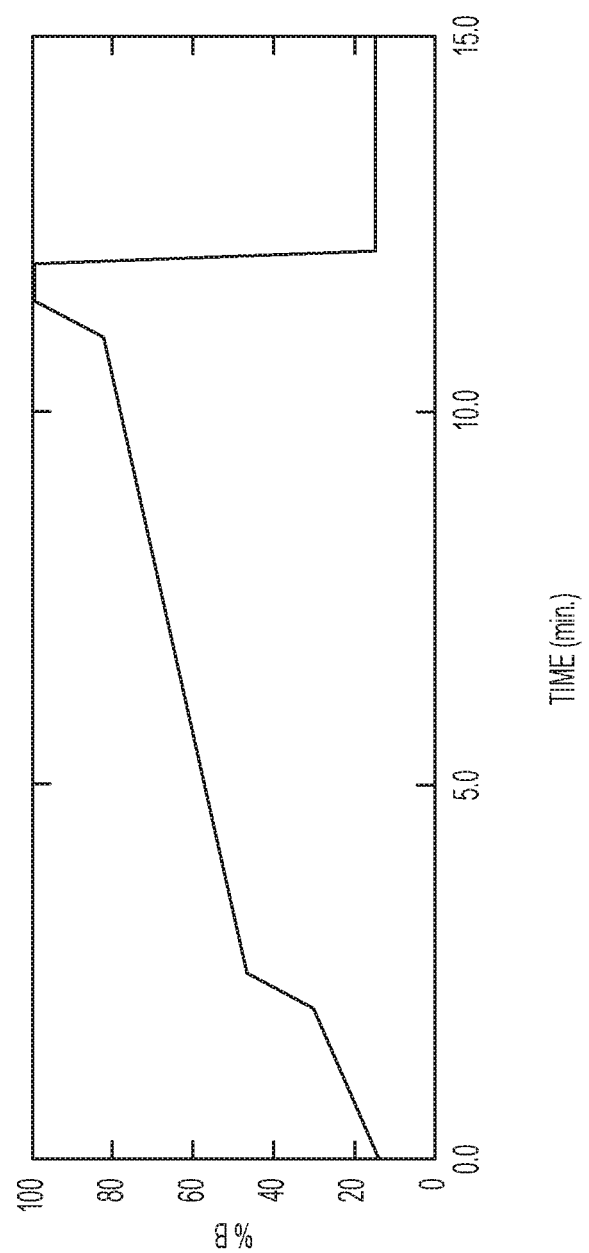
FIG. 8 is a graph of a gradient curve used in the LC part of an LC-MS/MS analysis for detection of metabolites and lipids in biological samples, according to an illustrative embodiment.

Column used: ACQUITY UPLC BEH C18, 100×2.1 mm, 1.7 μm particle size column from Waters
Pre-column used: VanGuard Acquity UPLC BEH C18 1.7 μm
Solvents used:
  A: 40% water, 60% acetonitrile, 10 mM ammonium formiate, 0.1% formic acid
  B: 10% acetonitrile, 85% isopropanol, 5% water, 10 mM ammonium formiate, 0.1% formic acid
Injection volume: 1 μL
Temperatures:
  Column temperature: 65° C.
  Auto sampler temperature: 10° C.
Gradient used
  Starting conditions: 15% B-85% A
  The rest of the gradient curve is shown in FIG. 8
Flow rate: 0.4 mL/min
Run time: 15 min
Equilibration time: 3 min The following is a description of the MS conditions used in the illustrative LC-MS/MS analysis protocol.

General conditions for the MS part of the analysis run are described in Table 7.

TABLE 7

| ESI + | | ESI − | | |
|---|---|---|---|---|
| CUR: | 40 | CUR: | 50 | MRM detection window: 60 sec |
| IS: | 4500 | IS: | −4500 | Target Scan Time: 0.1 sec |
| TEM: | 400 | TEM: | 400 | Resolution Q1: Unit |

TABLE 7-continued

| ESI + | | ESI − | | |
|---|---|---|---|---|
| GS1: | 40 | GS1: | 40 | Resolution Q3: Unit |
| GS2: | 50 | GS2: | 50 | Settling Time+: 50 msec |
| CAD: | Medium | CAD: | Medium | Settling Time+: 55 msec |
| EP | 10 | EP | −10 | MR Pause MRM: 5 msec |

Exemplary Amide-column Based Method

Figure 9:
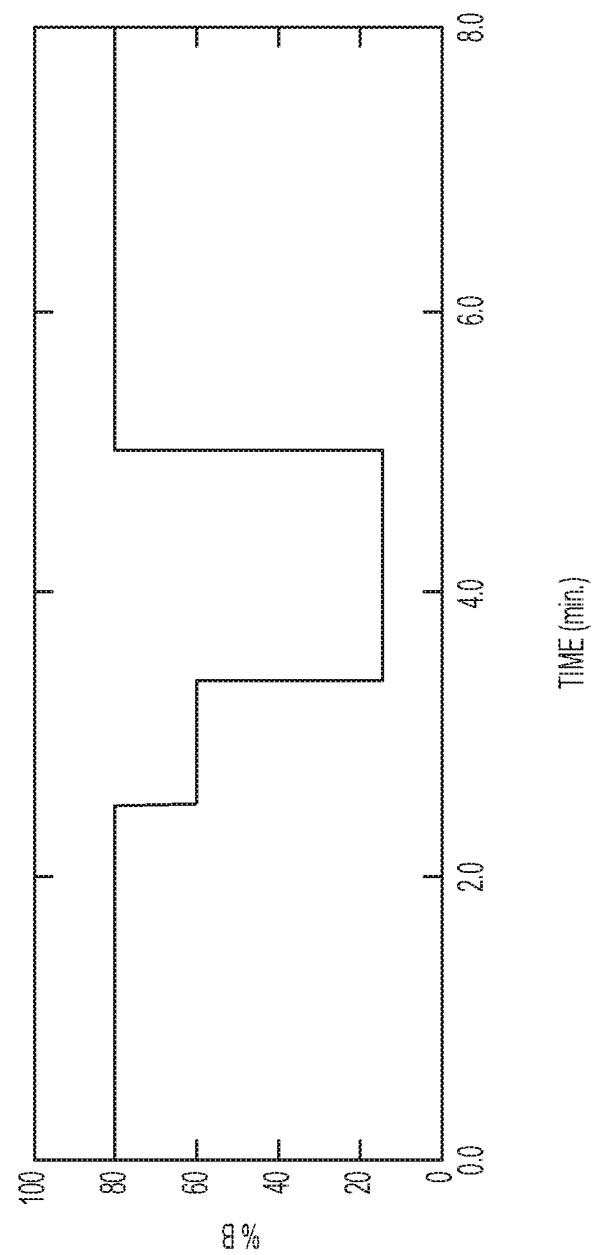
FIG. 9 is a graph of a gradient curve used in the LC part of an LC-MS/MS analysis for detection of metabolites and lipids in biological samples, according to an illustrative embodiment.

The following are the LC conditions used in an illustrative embodiment of an LC-MS/MS analysis protocol for markers using an amide-column based method:

Column Amide, 50×2.1 mm, 1.7 μm particle size
Pre-column used: VanGuard Acquity UPLC BEH Amide 1.7 μm
Solvents used:
  A: 70% water, 30% acetonitrile, 10 mM ammonium formate, 0.1% formic acid
  B: 95% acetonitrile, 5% water, 10 mM ammonium formate, 0.1% formic acid
Injection volume: 1 μL
Temperatures:
  Column temperature: 45° C.
  Auto sampler temperature: 10° C.
Gradient used:
  Starting conditions: 80% B-20% A
  The rest of the gradient curve is shown in FIG. 9
Flow rate: 0.4 mL/min
Times:
  Run time: 5 min
  Equilibration time: 3 min The following is a description of the MS conditions used in this illustrative LC-MS/MS analysis protocol.

General conditions for the MS part of the analysis run are described in Table 8.

TABLE 8

| ESI + | | ESI − | | |
|---|---|---|---|---|
| CUR: | 50 | CUR: | 50 | MRM detection window: 60 sec |
| IS: | 5000 | IS: | −4500 | Target Scan Time: 0.5 sec |
| TEM: | 550 | TEM: | 550 | Resolution Q1: Unit |
| GS1: | 60 | GS1: | 60 | Resolution Q3: Unit |
| GS2: | 65 | GS2: | 65 | Settling Time: 55 msec |
| CAD: | 9 | CAD: | 9 | MR Pause MRM+: 2 msec |
| EP | 10 | EP | −10 | MR Pause MRM−: 5 msec |

Amide-column based techniques require column maintenance. In the above exemplary amide-column based method, the following exemplary maintenance method steps may be used:

After every analysis batch: flush the column with a 60% water, 40% acetonitrile mix for 20 min at 0.4 mL/min. Repeat with 95% acetonitrile and 5% water mix. Store the column for short periods in a 95% acetonitrile and 5% water mix.

When column contamination is suspected (e.g., due to changes in peak shape, peak splitting, shoulders in peaks, change in run time), run a 10 minute gradient from 0%-100% water at 0.3 mL/min.

When column is not going to be used for periods longer than 4 days, run a gradient to 100% acetonitrile in order to flush aqueous solvent and store the column in 100% ACN at room temperature.

What is claimed:

1. A method for automated sample handling for extraction, detection and quantification of at least one metabolite biomarker in at least one biological sample, the method comprising the steps of:
   (a) thawing the at least one biological sample on a cooler block shaped and sized to hold the at least one biological sample;
   (b) mixing the at least one thawed biological sample;
   (c) following step (b), pipetting:
      (i) the at least one biological sample into at least one plate,
      (ii) at least one blank sample into the at least one plate, and
      (iii) at least one quality control sample into the at least one plate;
   (d) pipetting a solvent and an internal standard into (i) each of the at least one biological sample in the at least one plate, (ii) each of the at least one blank sample in the at least one plate, and (iii) each of the at least one quality control sample in the at least one plate;
   (e) shaking the at least one biological sample, the solvent, and the internal standard in the at least one plate;
   (f) incubating the at least one biological sample, the solvent, and the internal standard in the at least one plate on the cooler block;
   (g) centrifuging the at least one incubated biological sample in the at least one plate;
   (h) removing a first supernatant from the at least one centrifuged biological sample to at least one first analysis plate;
   (i) applying nitrogen flow to the first supernatant of the at least one biological sample in the at least one first analysis plate to obtain at least one dried biological sample;
   (j) resuspending the at least one dried biological sample in the at least one first analysis plate;
   (k) centrifuging the at least one resuspended biological sample in the at least one first analysis plate;
   (l) removing a second supernatant from the at least one centrifuged biological sample from step (k) in the at least one first analysis plate to at least one second analysis plate;
   (m) following step (l), placing the at least one second analysis plate in a metabolite separations/analytics subsystem; and
   (n) following step (m), generating at least one analysis report for the at least one biological sample.

2. The method of claim 1, wherein the at least one biological sample is 96 biological samples.

3. The method of claim 1, wherein the at least one biological sample is identified via a code and wherein the code is a member selected from a group consisting of: 2D code, 3D code, barcode, and RFID.

4. The method of claim 1, wherein each of the at least one biological sample is associated with a code and each code corresponds to clinical data.

5. The method of claim 1, wherein at least 8 biological samples are pipetted at a time.

6. The method of claim 1, wherein each of the at least one plate is a 96-well plate.

7. The method of claim 1, wherein the at least one quality control sample is prepared by mixing at least 5 µL of at least two biological samples.

8. The method of claim 1, comprising incubating the at least one biological sample, the solvent, and the internal standard in step (f) at about 4° C. for at least 15 minutes.

9. The method of claim 1, wherein the at least one incubated biological sample is centrifuged in step (g) and/or the at least one resuspended biological sample is centrifuged in step (k) at at least about 1000 g for at least 15 minutes.

10. The method of claim 1, wherein the nitrogen flow is applied at about room temperature for at least 80 minutes.

11. The method of claim 1, wherein the at least one dried biological sample from step (i) is resuspended in step (j) with $H_2O$:ACN.

12. The method of claim 1, wherein resuspending in step (j) is sequential aspirating and dispensing of the at least one dried biological sample at least 50 times.

13. The method of claim 1, wherein centrifuging the at least one resuspended biological sample in step (k) comprises centrifuging for at least 6 minutes.

14. The method of claim 1, wherein a third supernatant comprising at least 35 µL of the second supernatant from the at least one second analysis plate is moved to a final analysis plate.

15. The method of claim 14, wherein at least 10 µL of the third supernatant from the final analysis plate are transferred to a second final analysis plate where $H_2O$:ACN is added to dilute the transferred supernatant in the second final analysis plate.

16. The method of claim 1, wherein the metabolite separations/analytics subsystem comprises an HPLC and a mass spectrometer.

17. The method of claim 1, wherein the at least one first analysis plate and the at least one second analysis plate are stored at 4° C. until an analysis.

18. The method of claim 1, wherein the at least one analysis report is generated by a memory having instructions stored thereon, wherein the instructions, when executed by a computer processor, cause the computer processor to execute a script, wherein the script prescribes processing of the at least one biological sample via coordinated operation of a liquid handling arm, a plate handler; a code reader, the cooler block, a heater shaker unit, a centrifuge, a nitrogen drier, and the metabolite separations/analytics subsystem.

19. The method of claim 1, the method comprising, following the step of placing the at least one second analysis plate in the metabolite separations/analytics subsystem, performing one or more members selected from the group consisting of (i), (ii), and (iii), as follows:
   a reverse phase column based method;
   (ii) a flow injection analysis based method; and
   (iii) an amide-column based method.

20. The method of claim 19, wherein the reverse phase column based method is a member selected from the group consisting of a C18 reverse phase column method, a C18 50 mm reverse phase column method, a C18 100 mm reverse phase column method, a 50 mm reverse phase column method and a 100 mm reverse phase column method.

21. The method of claim 1, wherein step (b) comprises mixing the at least one thawed biological sample by repeated pipetting or shaking the at least one thawed biological sample.

22. The method of claim 1, wherein the solvent is methanol.

* * * * *